(12) United States Patent
Bordelon et al.

(10) Patent No.: US 9,759,714 B2
(45) Date of Patent: Sep. 12, 2017

(54) METHODS AND APPARATUS FOR NORMALIZING PATH LENGTH IN NON-INVASIVE GLUCOSE MONITORING

(71) Applicant: Socrates Health Solutions, Inc., Dallas, TX (US)

(72) Inventors: Michael Bordelon, Sugar Land, TX (US); Valentin Korman, Huntsville, AL (US)

(73) Assignee: Socrates Health Solutions, Inc., Dallas, TX (US)

( * ) Notice: Subject to any disclaimer, the term of this patent is extended or adjusted under 35 U.S.C. 154(b) by 41 days.

(21) Appl. No.: 14/995,519

(22) Filed: Jan. 14, 2016

(65) Prior Publication Data

US 2016/0209396 A1    Jul. 21, 2016

Related U.S. Application Data

(60) Provisional application No. 62/104,438, filed on Jan. 16, 2015.

(51) Int. Cl.
*G01J 4/00* (2006.01)
*G01N 33/49* (2006.01)
(Continued)

(52) U.S. Cl.
CPC ........... *G01N 33/49* (2013.01); *A61B 5/1455* (2013.01); *A61B 5/14532* (2013.01); *A61B 5/6815* (2013.01)

(58) Field of Classification Search
CPC ....................................................... G01J 4/00
(Continued)

(56) References Cited

U.S. PATENT DOCUMENTS

| 4,901,728 A | * | 2/1990 | Hutchison | ........... | A61B 5/14558 |
| | | | | | 356/368 |
| 5,009,230 A | * | 4/1991 | Hutchinson | ........ | A61B 5/14558 |
| | | | | | 356/368 |

(Continued)

OTHER PUBLICATIONS

Smith, John L. "The Pursuit of Noninvasive Glucose: "Hunting the Deceitful Turkey"" Feb. 26, 1996. World Wide Web. Jul. 3, 2015. <http://www.mendosa.com/noninvasive_glucose.pdf>.

(Continued)

*Primary Examiner* — Roy M Punnoose
(74) *Attorney, Agent, or Firm* — The Courtney Firm (57) ABSTRACT

Methods and apparatus for normalizing path length in an optical system for non-invasive glucose concentration. A method arrangement includes providing an optical energy source spaced from a first photo-detector by a sensing area; transmitting energy from the optical energy source onto the first photo-detector; storing a first reading corresponding to the light intensity observed by the first photo-detector; subsequently, introducing a container of solution including an optically active substance into the sampling area; transmitting energy from the optical energy source through the container in the sampling area and onto the first photo-detector; storing a second reading corresponding to the light intensity observed by the first photo-detector; determining a ratio of the first reading to the second reading; and determining a path length L by computing $L=\ln(\text{ratio})/\mu$ where $\mu$ is an absorption constant of the optical energy in the solution and container. Additional arrangements are disclosed.

20 Claims, 3 Drawing Sheets

(51) Int. Cl.
*A61B 5/145* (2006.01)
*A61B 5/1455* (2006.01)
*A61B 5/00* (2006.01)

(58) Field of Classification Search
USPC .................................................. 356/39, 364
See application file for complete search history.

(56) References Cited

U.S. PATENT DOCUMENTS

| | | | | | |
|---|---|---|---|---|---|
| 5,383,452 | A | * | 1/1995 | Buchert | A61B 5/14558 |
| | | | | | 600/347 |
| 5,477,327 | A | * | 12/1995 | Bergman | G01N 21/21 |
| | | | | | 356/367 |
| 8,743,355 | B2 | * | 6/2014 | Korman | G01N 21/21 |
| | | | | | 356/39 |
| 9,101,308 | B2 | * | 8/2015 | Korman | G01N 21/21 |
| 9,320,463 | B2 | * | 4/2016 | Korman | G01N 21/21 |
| 2004/0238361 | A1 | * | 12/2004 | Shulman | G01N 21/21 |
| | | | | | 204/452 |
| 2014/0104596 | A1 | * | 4/2014 | Korman | G01N 21/21 |
| | | | | | 356/39 |
| 2014/0268103 | A1 | * | 9/2014 | Korman | G01N 21/21 |
| | | | | | 356/39 |
| 2015/0342507 | A1 | * | 12/2015 | Korman | G01N 21/21 |
| | | | | | 600/316 |
| 2016/0206232 | A1 | * | 7/2016 | Bordelon | A61B 5/1455 |
| 2016/0213292 | A1 | * | 7/2016 | Korman | G01N 21/21 |

OTHER PUBLICATIONS

Danaei, Goodarz; et al. "National, Regional, and Global Trends in Fasting Plasma Glucose and Diabetes Prevalence since 1980: Systematic Analysis of Health Examination Surveys and Epidemiological Studies with 370 Country-Years and 2.7 Million Participants." www.thelancet.com Jul. 2011: 31-40. vol. 378, No. 9785. World Wide Web, Jul. 23, 2015. http://www.thelancet.com/pdfs/journals/lancet/PIIS0140-6736(11)60679-X.pdf.

* cited by examiner

METHODS AND APPARATUS FOR NORMALIZING PATH LENGTH IN NON-INVASIVE GLUCOSE MONITORING

RELATED APPLICATIONS

The present application claims the benefit of priority under 35 U.S.C. §119(e) to U.S. Provisional Application Ser. No. 62/104,438 filed Jan. 16, 2015, entitled "Methods and Apparatus for Normalizing Path Length in Non-Invasive Glucose Monitoring," which application is hereby incorporated by reference herein in its entirety.

TECHNICAL FIELD

The embodiments relate generally to the use of the optical rotation (θ) property of the glucose molecule to perform non-invasive glucose monitoring.

BACKGROUND

Diabetes mellitus is a group of diseases causing abnormal blood sugar levels over a prolonged period of time. Diabetes is a result of either the pancreas not producing enough insulin, or the failure of the cells to respond to the insulin produced. As of November 2014, studies estimate that around 347 million people worldwide have the disease, *Lancet,* 378(9785):31-40 (2011). The World Health Organization (WHO) projects that diabetes will be the seventh leading cause of death by 2030.

Diabetes has been recognized since around 1500 BCE, but until only 50 years ago, accurate glucose monitoring required individuals to visit healthcare professionals. As management of the disease focuses on monitoring of glucose and finding a lifestyle that better controls glucose levels, visiting a doctor's office for every test is inefficient and ineffective. More accurate monitoring systems were developed in the 1960's, allowing individuals to test at home. Since that time, glucose monitors have improved from biochemical reactions in which a color change would be visually compared to a color chart, to electrochemical reactions in which a reaction with the glucose in the blood would be measured and read digitally. In the last 50 years, tests have gotten faster (from over a minute to just a few seconds) and easier (early tests required washing and blotting test strips), and lancets have evolved from steel strips with a point to spring-loaded needles. These changes have made home testing better, but the fact remains that drawing blood for testing is not only a potential health hazard, but also carries with it social stigma, pain, produces medical waste that needs proper disposal, and the patient has to bear the cost of one time use test strips.

Research has focused on a non-invasive or minimally invasive monitoring system since at least the mid 1970's. These systems have approached the problem through numerous medical monitoring techniques, each presenting its own set of drawbacks U.S. Pat. No. 8,743,355, (the '355 Patent), entitled "Simple Sugar Concentration Sensor and Method," issued Jun. 3, 2014, which is hereby incorporated by reference herein in its entirety, discloses optical sensing of the angular rotation of optical energy passed through a sample including a sugar, for example, glucose in a fluid. In particular the '355 Patent discloses using photosensitive detectors to sense the rotation of polarized light that passes through a sample, for example, through human tissue including blood. As described in the '355 Patent, the angular rotation of the optical energy passing through a sugar containing solution is described by the relation:

$$\Theta = \alpha \times L \times C \quad \text{(Equation 1)}$$

Where L is a path length, C is the sugar concentration in the fluid, and α is a rotation constant. The constant α depends on the wavelength of the light, the type of sugar molecule, and the fluid in which the sugar is dissolved.

The '355 Patent describes optical measurements made on a portion of the human ear using polarizers to create polarized light, and a difference measurement taken between two photosensitive detectors, one with a polarizer, and one without. However, using the prior known approaches that are described in the '355 Patent, the readings obtained require additional accuracy and an increase in reproducibility to enable a practical glucose meter for patient use.

The inventors of the present application have further researched the approach of the '355 Patent and related non-invasive glucose measurements and found that the prior known approaches described to date lack the accuracy, reproducibility in results, efficiency and ease of use needed to provide a practical commercial non-invasive glucose monitor.

Improvements are therefore needed in non-invasive glucose monitoring in order to address the deficiencies and the disadvantages of the prior known approaches. Solutions are needed that reduce the cost and complexity of the monitor system and which can accurately measure changes in blood glucose concentration.

SUMMARY

A system and methods for normalizing the optical path length in non-invasive glucose monitoring are provided.

In an aspect of the present application, a method for performing non-invasive optical measurements includes: providing an optical energy source spaced from a first photo-detector by a sensing area; transmitting energy from the optical energy source through a first polarizer at a reference polarization angular position across the sensing area and through a second polarizer at the same reference polarization angular position and onto the first photo-detector, storing a first reading corresponding to the light intensity observed by the first photo-detector; subsequently, introducing a container of solution into the sampling area, the solution including an optically active substance; transmitting energy from the optical energy source across the first polarizer, the sensing area including the container, through the second polarizer, and onto the first photo-detector; storing a second reading corresponding to the light intensity observed by the first photo-detector; determining a ratio of the first reading to the second reading; and determining a path length L by computing L=ln(ratio)/μ where μ is an absorption constant of the optical energy in the solution and container.

In a further aspect of the present application, the above method is performed and further includes: transmitting optical energy from the optical energy source through the first polarizer and through the container and through a third polarizing device onto a second photo-detector; receiving the optical energy from the optical energy source through the first polarizer and onto a reference photo-detector; determining a change in polarization by observing a difference between the light intensity received at the second photo-detector and the light intensity at the reference photo-detector, the difference corresponding to an angle of rotation Θ; and computing the concentration C of an optically active compound in the solution as: $C=(\alpha*(\ln(\text{ratio})/\mu)/\Theta)$, where $\alpha$ is a rotation constant.

In yet another aspect of the present application, an apparatus for non-invasive concentration measurement of a sugar in a solution is provided, which includes: an optical energy source spaced from a first photo-detector by a sensing area; a first polarizer placed between the optical energy source and the sensing area and configured to polarize at a first reference polarization angular position; a first optical steering device between the sensing area and the first photo-detector, the first optical steering device outputting a reference signal to the first photo-detector and outputting a second signal; a second photo-detector placed to receive the second signal; a second polarizer placed between the first optical steering device and the second photo-detector to receive the second signal and configured to polarize at the same first reference polarization angular positon and to output a polarized light signal; wherein the first photo-detector and the second photo-detector are arranged to receive the reference signal and the polarized light signal from the optical steering device.

Additional alternative arrangements are also described to form additional aspects of the present application.

BRIEF DESCRIPTION OF THE DRAWINGS

For a more complete understanding of the illustrative embodiments described herein and the advantages thereof, reference is now made to the following descriptions taken in conjunction with the accompanying drawings, in which.

Corresponding numerals and symbols in the different figures generally refer to corresponding parts unless otherwise indicated. The figures are drawn to clearly illustrate the relevant aspects of the arrangements and are not necessarily drawn to scale.

DETAILED DESCRIPTION

The making and using of example illustrative arrangements are discussed in detail below. It should be appreciated, however, that the various arrangements that form aspects of the application provide many applicable inventive concepts that can be embodied in a wide variety of specific contexts. The specific arrangements discussed are merely illustrative of specific ways to make and use the various aspects of the present application, and do not limit the scope of the specification, or any appended claims.

Figure 1:
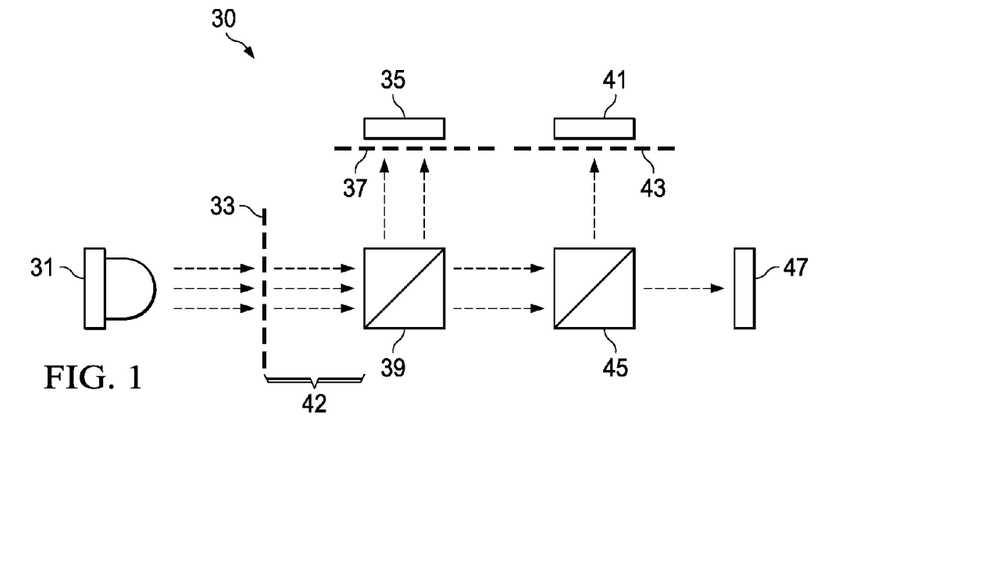
FIG. 1 depicts in a simple block diagram the components of a non-invasive glucose monitoring system using the property of optical rotation.

FIG. 1 depicts in a simple illustration the components of a non-invasive glucose monitoring system 30 which can detect changes in concentration using the property of optical rotation of light passed through a solution including a sugar, such as glucose. Component 31 represents an illumination source. In an example arrangement, a light emitting diode (LED) can be used as component 31 to produce optical energy in the form of signal light. In a non-limiting example, a red LED can be used as component 31. In another example, an alternate light source, such as a laser, can be used. Near-infrared light can also be used for component 31. The optical energy from component 31 can vary in wavelength but should be selected so that the light is affected by the presence of a sugar in a solution, and a substantial amount of the light should be able to pass through the container or tissue holding the solution. In an example implementation LEDs of between 600 and 700 nanometers are used. Component 33 represents a polarizer at a first reference polarization angle. In an example implementation the polarizer 33 was at 0° rotation. Component 39 represents an optical steering device for directing the light in multiple directions. In one example arrangement that is an aspect of the present application, an optical beam splitter can be used to create two light paths each having the light transmitted through the sensing area 42 and/or a sample placed in sensing area 42. One path is for a polarized signal and one is for a reference signal. In additional alternative arrangements that are contemplated herein, the optical steering device 39 can be formed using prisms, mirrors, dichroic plates, and the like. The various arrangements can be used to direct light from the sensing area to the photo-detector 35 and to the second optical steering device 45.

Component 47 represents a photosensitive detector or photo-detector, such as for a non-limiting example, a photodiode, used to convert the reference signal light into a current corresponding to incident light received. Component 37 represents a polarizer at, for example but not limited to, approximately 45° rotation for outputting polarized signal light. Component 35 represents a second photo-detector or photodiode used to convert the polarized signal light into a second current corresponding to the polarized light received.

In addition, in FIG. 1 a third polarizer 43 is shown. This polarizer can be a simple film polarizer although as alternative arrangements, additional polarizers can be used, and in one example polarizer 43 can be a polarizer at the same reference polarization angle to match the polarizer 33 at the illumination source 31. In one example implementation both polarizers 43, 33 were at 0°. As an alternative to the 0° polarizers, linear polarizers can be used. A third photo-detector 41 is used to measure light for an absorption measurement. The use of the polarizers 33, 43 at both the illumination source 31 and the absorption photo-detector 41 can ensure that the light measured at photo-detector 43 is unscattered light from the polarizer 33, and the measurement is not for ambient or scattered light. However, in an alternative arrangement presented below, the polarizer 43 is not present and the photodetector 47 is used for absorption measurements.

FIG. 1 illustrates in a non-limiting example arrangement that is an aspect of the present application, a system 30 in use. In operation, an illumination source, in this example, a light emitting diode (LED) 31 emitting light at a constant wavelength through a polarizer 33 aligned, in this non-limiting example, at a reference polarization angle of 0°. The polarized light passes through a sensing space 42 which can contain, for example, a tissue sample including blood. Alternatively a reference sample or a sample in a container such as a tube can be placed in the sensing space 42. The light transmitted through the sensing space 42 and/or sample is passed through to an optical beam splitter 39, which directs approximately 50% of the light through a polarizer 37 which is at approximately 45°. The polarized light is then absorbed by a photodiode 35 which provides the polarized signal. The other approximately 50% of the light exits the optical steering device, such an optical beam splitter, 39 and traverses a second optical steering device, which can also be an optical beam splitter, 45, and is absorbed by a second photo-detector or photodiode 47 with no additional polarization. This second photodiode 47 provides a reference signal.

In one method that forms an aspect of the present application, in operation the system 30 can be calibrated to a baseline glucose concentration so that a voltage difference corresponding to the difference in intensity of the light received at the two photo-detectors 35 and 47 is due to a change in polarization of the light through the sample, and this change in polarization correlates to the change in glucose concentration. The use of the approximately 45 degree polarizer 37 makes the change in rotation (caused by a change in concentration away from a baseline concentration) move the polarization angle along the linear portion of a sine wave. This makes detecting the change in rotation easier (because the change in rotation moves the angle in a linear part of the curve) than it would be at the crest, or trough, of the sine wave. Additional circuitry (not shown in FIG. 1 but described and illustrated below) can be provided to adjust the signal strength using gain for one or both photo-detectors 35, 47 to make the difference between the voltage signals corresponding to the incident light on the photo-detectors correlate to the change in rotation from the baseline concentration. A subtractor circuit such as an analog operational amplifier or a comparator can be used to form the difference. Transimpedance amplifiers can be used to create voltages corresponding to the current outputs from the photodiodes 35 and 47, for ease of use in forming the difference between them. Analog to digital circuitry, and digital processors, shown further below, can be used to perform calculations based on the signals from the photo-detectors 35, 47.

System 30 can be calibrated before taking concentration measurements. Calibration can be performed by measuring the voltage difference due to optical rotation using a sample with a known sugar or glucose concentration. As an alternative, a calibration can be performed for system 30 by using a measured glucose concentration for a patient obtained more or less contemporaneously by using a glucose blood meter of the known prior art, and correlating the measurement to a baseline measurement obtained using system 30. Subsequent measurements made using system 30 can then detect a voltage difference that corresponds to a change in the rotation of polarized light moving through the tissue or sample, and the amount of change in the rotation can then be correlated to the amount of change in the glucose concentration. In another alternative arrangement that forms another aspect of the present application, when large changes in the glucose concentration from the baseline concentration are detected, an indicator can be activated. Note the difference voltage detected due to concentration change can be detected for increasing and decreasing sugar or glucose concentrations, so both hyperglycemic and hypoglycemic conditions can be detected. After receiving an indicator from the system, the user or patient can then take appropriate measures to manage their blood glucose.

Figure 2:
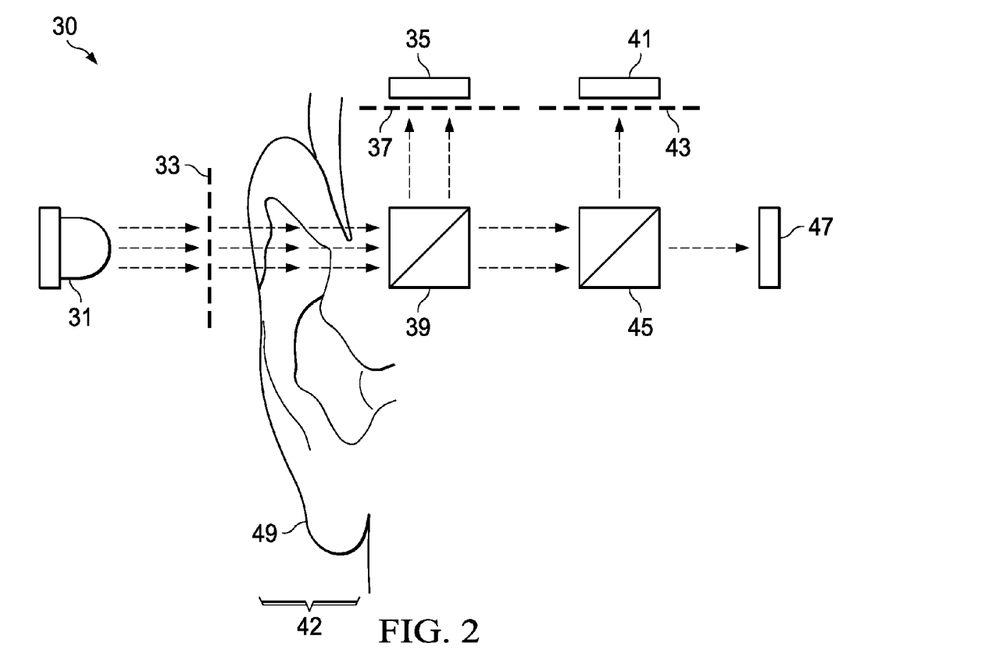
FIG. 2 illustrates the use of the system in FIG. 1 in an example application for taking measurements applied to the tissue of the human ear.

In FIGS. 1 and 2, additional features are obtained by the use of the second optical steering device 45, which can be implanted for example using a second optical beam splitter. In FIG. 2, optical steering device 45 is placed between the first optical steering device 39 and the reference photo-detector 47. The attenuation seen by the polarization photodiode 35 is a 50% loss due to the first beam splitter 39, and a 50% loss due to the approximately 45 degree polarizer 37. Thus the light incident on the photo-detector 35 is reduced to 25% of the intensity from the polarizer 33.

By using the second optical steering device 45 between the linear polarizer 33 and the reference photo-detector 47, the two light paths are close to a balanced condition. The light incident on the photo-detector 47 is also reduced by 50% at the first optical steering device, for example a beam splitter, 39 and again by 50% by the second beam splitter 45. The light incident on the reference photo-detector 47 is therefore also 25% of the light intensity from the linear polarizer 33.

The second optical steering device 45 also provides another output signal that is convenient for use in making additional measurements using the absorption photo-detector 41 as described below. It should be noted, however, that the use of the second optical steering device such as a beam splitter 45 is optional, and alternative arrangements can be used to direct light to the reference photodiode 47 and to an absorption photo-detector 41, while still forming arrangements contemplated by the inventor and which fall within the scope of any appended claims. For example, gain adjustments can be used to compensate that voltage corresponding to the photo-detector 35 for the attenuation in the path, instead of using the second optical steering device 45.

FIG. 2 illustrates the use of the system arrangement 30 illustrated in FIG. 1 in an example application. In this example, the measurement using system 30 is applied to the tissue of the helix or anti-helix of a human ear 49. However, this is but one example and the arrangements and the application are not so limited. Other tissue sites that have a significant blood component such as the other portions of the human ear, the lobe of the human ear, the flesh between the index finger and the thumb, or flesh between toes, could also be used. The anti-tragus and tragus regions can be used.

As in FIG. 1, in FIG. 2 component 31 represents an illumination source. In an example arrangement, a light emitting diode (LED) can be used as component 31 to produce optical energy in the form of signal light. The ear 49 is in the sensor space 42 for this example application. Component 33 represents a polarizer, in an example implementation, this polarizer can be at a reference polarization angular position at 0° rotation. Component 39 represents an optical steering device such as, but not limited to, an optical beam splitter used to create two light paths each having the light transmitted through a sample, one for a polarized signal and one for a reference signal. Component 47 represents a photosensitive detector or photo-detector, such as for a non-limiting example, a photodiode, used to convert the reference signal light into a current corresponding to incident light received. Component 37 represents a polarizer at, for example but not limited to, a 45° rotation, or an approximately 45° rotation. Component 35 represents a second photodiode used to convert the polarized signal light into a second current corresponding to the polarized light received.

In addition, a third polarizer 43 is shown. This polarizer can be a simple film polarizer and in this non-limiting, illustrative example is a 0° degree polarizer to match the polarizer 33 at the illumination source 31. Other matching polarization angular positions can be used. A third photodetector 41 is used to measure light for an absorption measurement. The use of the matched polarizers at both the illumination source 31 and the absorption photo-detector 41 ensure that the light measured is unscattered light from the polarizer 33, and the measurement is not made on ambient or scattered light. In an alternative arrangement described with respect to FIG. 6, unpolarized light is used for certain measurements.

For use in a practical glucose meter device, it has been discovered by the inventors of the present application that the system 30 requires additional accuracy. Repeating Equation 1, above, the angular rotation for light passing through a solution including sugar is given by:

$$\Theta = \alpha \times L \times C \quad \text{(Equation 1),}$$

where $\alpha$ is the rotation constant for glucose, L is the path length, and C is the concentration of the glucose.

The inventors of the present application have determined that the prior known solutions for determining the concentration C from the voltage difference measured due to a change in rotation, $\Theta$, lack sufficient accuracy and reproducibility for use in a practical glucose meter. It has been further discovered that the observed measurement errors can be due, at least in part, to the fact that in the prior known solutions the optical path length L is not sufficiently constrained to permit accurate measurements of the rotation corresponding to changes in concentration, C. In order to obtain useful and reproducible results, the path length L should be accurately measured and for still better results, in has been discovered that this measurement can also be performed contemporaneously with the voltage difference measurement. The various arrangements provided herein form aspects of the present application that normalize the path length L. This is in sharp contrast to the prior approaches, where using a fixed or predetermined value for path length L failed to produce reliable and reproducible results.

A novel method for making glucose measurements using only optical properties has been discovered that overcomes the various limitations of the prior known solutions.

Absorption of light transmitted through a solution may be determined using Beer's law, as expressed in Equation 2:

$$A = -\ln\left(\frac{I}{Io}\right), \quad \text{(Equation 2)}$$

Where I is the light successfully transmitted through the material, and Io is the light transmitted through free space The absorption A may further be described as the product of an absorption constant of the material for the optical energy used, $\mu$, and the length L of the optical path traversed in the material, e.g.:

$$A = \mu \times L, \quad \text{(Equation 3),}$$

where L is the path length and $\mu$ is the absorption constant.

In the arrangements that form various aspects of the present application an absorption measurement is made in conjunction with the optical rotation measurement. Since the voltage difference due to a change in the rotation $\Theta$ observed is described by Equation 1 as a product of two variables, C and L, and of $\alpha$, which is a rotation constant for the chiral material, there are still two unknown variables, the concentration C which is needed for the meter functions, and the path length L.

Using the Beers law relationship, the two equations can be solved for the concentration C by algebraic manipulation and substitution:

$$L = \frac{A}{\mu} = \frac{\ln\left(\frac{Io}{I}\right)}{\mu}, \quad \text{(Equation 4).}$$

And then, by substituting for L in Equation 1, and solving for concentration C:

$$C = \alpha x \left(\frac{\left(\frac{\ln\left(\frac{Io}{I}\right)}{\mu}\right)}{\theta}\right), \quad \text{(Equation 5).}$$

Note that Equation 5 allows a measurement of the rotation $\Theta$ and a measurement of the absorption of light in free space, Io, and the light that is transmitted through the sample, I, to completely describe the unknown concentration, C. Length L in Equation 1 is now replaced by an absorption measurement obtained by additional optical measurements, and thus Equation 5 contains only $\Theta$ and physical constants, in addition to the intensity measurements for I and Io.

Equation 5 may be specifically written for a blood glucose measurement taken at the human ear, as:

$$Cgluclose = \alpha X \left(\frac{\left(\frac{\ln\left(\frac{Io}{Iear}\right)}{\mu}\right)}{\theta}\right), \quad \text{(Equation 6)}$$

where Io is the freespace light intensity, Iear is the light transmitted through the ear, $\alpha$ is the rotation constant for glucose and $\Theta$ is the rotation measurement.

The absorption constant $\mu$ can be calibrated by taking a reading for each person using the sensor at the ear, using an independently measured glucose concentration, for example. In the method arrangements that form aspects of the present application, an absorption photo-detector such as 41 in FIGS. 1 and 2 is provided to collect voltages corresponding to the light intensity at the photo-detector 41 for the freespace Io, and voltages corresponding to light intensity for an ear or other container in the sensing area, for example. Alternatively a polarizer at a reference polarization angle, such as for example 0°, could be placed temporarily in front of the reference photo-detector 47 for the absorption measurements, and then removed for the difference measurements. These variations form additional alternative arrangements that are also contemplated herein as additional aspects of the present application.

Figure 3:
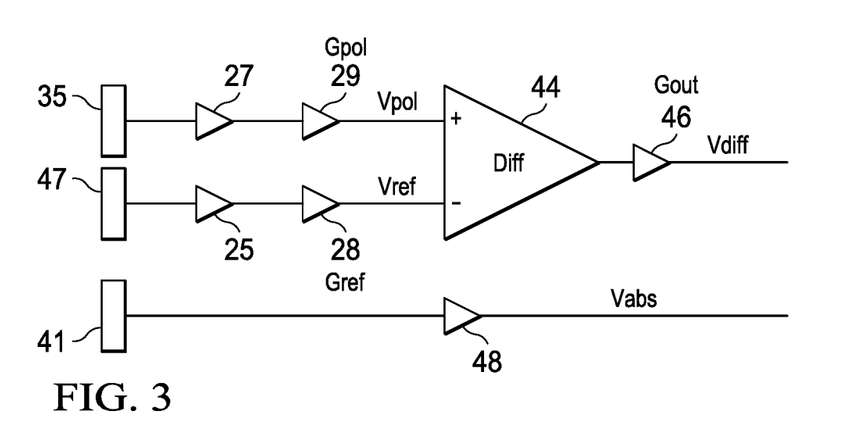
FIG. 3 illustrates in a circuit block diagram an example analog circuit for use with the arrangements that form aspects of the present application.

FIG. 3 depicts in a simple block diagram an example analog circuit for use with the various arrangements. In FIG. 3, the circuitry receives signals from photo-detector 35, the photo-detector behind the 45 degree polarizer 37 in FIG. 2, photo-detector 41, the photo-detector behind the reference polarizer, and the third photo-detector 47, as shown in FIGS. 1 and 2.

In FIG. 3, the output of photo-detector 47 is coupled to a transimpedance amplifier 25 for obtaining a voltage that corresponds to the current output by photo-detector 47 in response to light received. A gain stage 28 provides a gain, Gref, on the reference signal. As an initial setting, this gain can be unity or "1."

Photo-detector 35 is the photo-detector behind the 45 degree polarizer in FIGS. 1 and 2. In FIG. 3, the current from photo-detector 35 is input to a transimpedance amplifier 27 to form a voltage corresponding to the light sensed by photo-detector 35. The voltage is then coupled to a gain stage 29 with gain Gpol. This gain stage 29 and the gain stage 28 can be implemented by an operational amplifier, or a locking amplifier, or any other positive gain amplifier. As an initial setting, this gain stage is used to compensate for the loss from the polarizer 37 in FIGS. 1 and 2 and thus, can initially be set to about 2 for a typical polarizer with 50% loss. The output of the gain stage 29, with gain Gpol, is a voltage, Vpol. The two voltages Vref and Vpol are then input to a comparator or subtractor 44 that forms a difference voltage. The comparator 44 can be implemented using an operational amplifier circuit, for example. The output signal from comparator 44 is a voltage difference that corresponds to a change in concentration causing a rotation in the light passing through the solution, and can be a very small voltage signal. A gain stage 46 then increases this signal to form an output voltage, Vdiff. The gain input Gout allows additional gain adjustment at the output.

The voltage, Vdiff, which by means of the subtraction operation of comparator 44 is free from common mode noise and light intensity noise sources seen by both photo-detectors 35 and 47, corresponds to the change in light intensity due to the chiral rotation in the solution light path, such as glucose. By measuring the difference voltage, Vdiff, the change in the rotation angle, θ, can be determined, and the concentration (or change from a baseline concentration) can then be determined using Equation 1.

In FIG. 3, the output of the photo-detector 41 can be used for making absorption measurements. A transimpedance amplifier 48 receives the current corresponding to the light on the photo-detector 41 and outputs a corresponding voltage Vabs.

Figure 4:
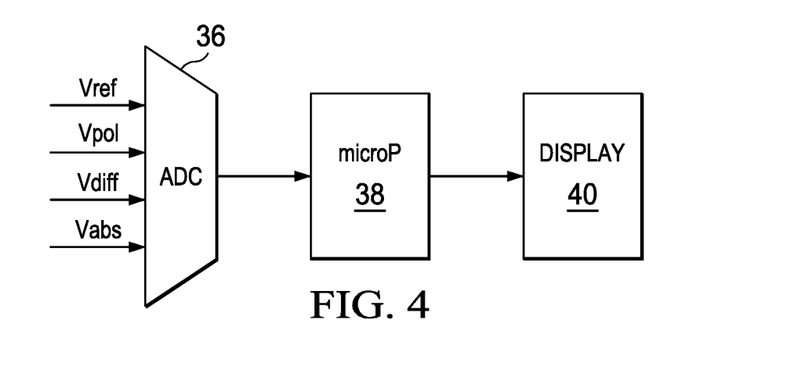
FIG. 4 illustrates in a circuit block diagram an example digital circuit for use with the arrangements that form aspects of the present application.

FIG. 4 depicts in a simple block diagram a digital circuit for use with the various arrangements. In FIG. 4, a digital portion of the system that can be used to determine the concentration or a change from a baseline concentration. The analog signals from FIG. 3, the reference voltage, Vref, the polarized signal voltage, Vpol, and the difference voltage, Vdiff, and the absorption voltage Vabs are input into an analog to digital converter block 36, which can be implemented using any of a variety of commercially available analog to digital converters. The digital outputs are then input to a microprocessor 38 which includes on board storage for the data values and storage for executable programs. By programming the microprocessor, the calculations needed to compute the concentration as shown in Equations 1-6, for example, can be performed. The microprocessor 38 can then output values for display to a monitor or indicator display 40. In addition the absorption measure voltage Vabs can be used with the digital microprocessor to determine the ratio of free space light intensity to the light through a sample, to determine the path length L.

Figure 5:
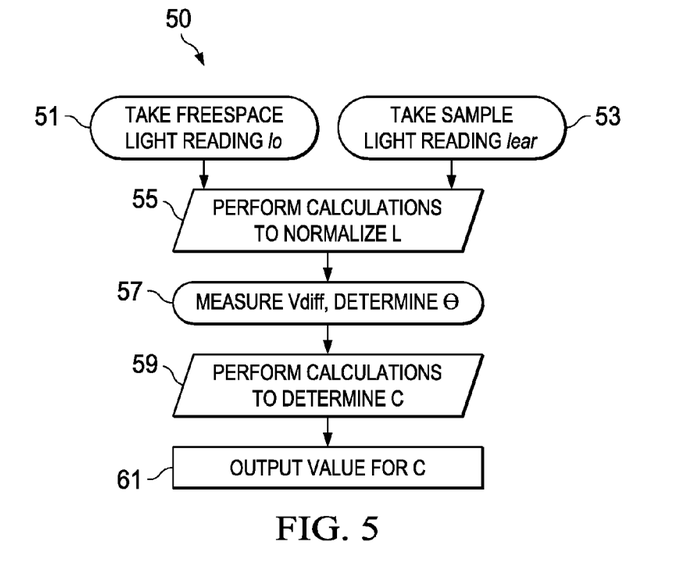
FIG. 5 illustrates in a flowchart a novel method of the present application performed for normalizing the path length of light through the system of FIGS. 1 and 2 for use in determining glucose concentration.

FIG. 5 depicts in a flowchart 50 an example method arrangement that forms another aspect of the present application. In FIG. 5, at step 51, optical measurements are taken with nothing in the sensing space of the system of FIG. 1, for example, to determine Io using the absorption photo-detector. At step 53, which is performed independently of step 51 and can be done before, or after, step 51, a reading of the light transmitted through the sample, here labeled Iear, is taken using the absorption photo-detector. At step 55, the length L is determined by performing the calculation in Equation 4, for example. At step 57 the system 30 of FIG. 1 is used to measure the difference voltage that indicates the change in the rotation angle Θ. At step 59, the concentration (or, a change in concentration relative to a baseline value) is determined by performing the calculation as in Equation 6. Note that the sequence of steps performed is not necessarily order dependent, that is, the measure of Vdiff corresponding to a change in rotation Θ in step 57 can be performed after step 55, or at the same time as step 55. After the concentration, or the relative change in concentration, is determined by the calculation in step 59, the value for C is output at step 61. Alternatively, an indicator that the change is within a normal range, or an indicator that the concentration is high, or low, can be output for ease of use by a patient.

An additional method arrangement for use of the system in FIGS. 1 and 2 with the normalized path length method to monitor glucose is to use the steps described above performed to determine the current glucose concentration. The result is then presented to the user. This result can be a relative change in concentration, or a measured concentration. If the current value for blood glucose concentration is within a normal range, (or if the change from a baseline concentration is small enough to place the concentration within a normal range) then no further action is needed. If however the glucose concentration is outside a predetermined normal range, that is, greater or lesser than a predetermined range, or if a change in concentration from a baseline value is greater than, or lesser than, a predetermined normal range, then the user can be, for example, directed to take additional steps. The user could perform an additional test with a traditional glucose meter. In this fashion, for many situations, the non-invasive tests described above are performed and when the blood glucose concentration is in a given range from a baseline concentration, no further action is taken by the patient. In an example where the patient's blood glucose concentration is higher or lower than a normal range, then the patient can decide to perform a second test to obtain a precise concentration reading. In this manner the patient is freed from using the traditional stick meter for many tests that are presently performed and if the readings are within a normal range using the novel methods described above, the patient does not have to endure the pain or the inconvenience of the stick test.

Returning to Equation 4 above, it is noted that while the use of the reference angle polarizers between the illumination source such as an LED and the absorption photodetector can assist in reducing or eliminating measurement of unwanted ambient or stray light, the polarizers are not required for the length measurement, as can be seen from examining the terms:

$$L = \frac{A}{\mu} = \frac{\ln\left(\frac{Io}{I}\right)}{\mu},$$ (Equation 4).

Figure 6:
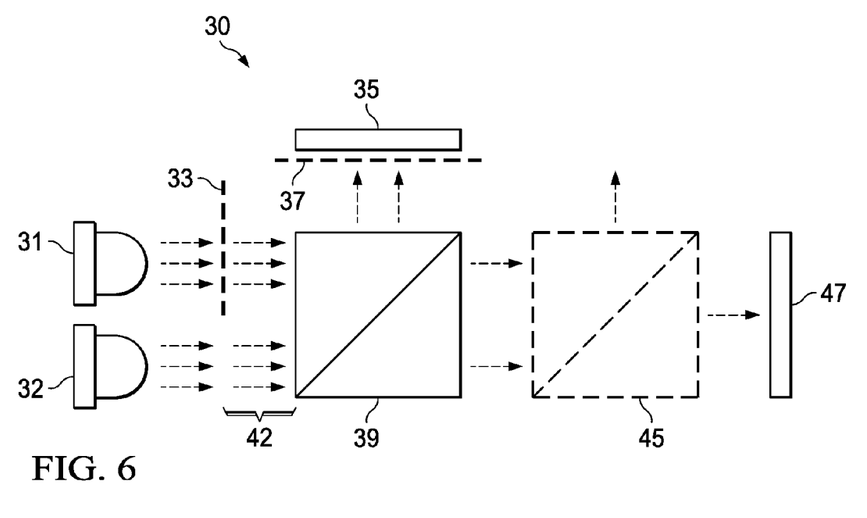
FIG. 6 illustrates an alternative apparatus arrangement that forms an additional aspect of the present application.

FIG. 6 illustrates an alternative arrangement that uses unpolarized light for the length intensity measurements. As in FIG. 1, in FIG. 6 component 31 represents a first illumination source. In an example arrangement, a light emitting diode (LED) can be used as component 31 to produce optical energy in the form of signal light. In FIG. 6, a second illumination source 32 is provided and is used independently of component 31, and can also be an LED or other light emitting component. The light from either LED 31 or 32 traverses sensor space 42. Component 33 represents a polarizer, in an example implementation, this polarizer can be at a reference polarization angular position for 0° rotation. In contrast to the arrangement of FIG. 1 or 2, in FIG. 6 the polarizer 33 only impacts light emitted from LED 31, and not from LED 32. Thus light emitted from LED 32 into the sensor space 42 is not polarized. As in FIGS. 1 and 2 above, component 39 represents an optical steering device such as, but not limited to, an optical beam splitter used to create two light paths each having the light transmitted through a sample, one for a polarized signal and one for a reference signal. Also, component 47 represents a photo-sensitive detector or photo-detector, such as for a non-limiting example, a photodiode, used to convert the reference signal light into a current corresponding to incident light received. In this arrangement, component 47 will be used to detect unpolarized light for the absorption measurement used to normalize the length of the path. Component 37 represents a polarizer at, for example but not limited to, a 45° rotation, or an approximately 45° rotation. Component 35 represents a second photodiode used to convert the polarized signal light into a second current corresponding to the polarized light received.

Unlike the arrangement in FIGS. 1 and 2, no third photodetector is used in FIG. 6. Instead, the reference photodetector 47 is used both for the absorption measurements using unpolarized light from component 32, and also for the rotation measurements using polarized light from component 31 and polarizer 33. As discussed above, the use of the optical beam splitter 45 is optional. This component is thus shown in a dashed line form, to indicate it may not be present. When it is present, optical beam splitter 47 is used to provide a simple apparatus to normalize the attenuation of light between the component light source 31 and the two photodetectors 35 and 47, as was discussed above. However other signal compensation schemes can be used to adjust for signal attenuation, and the optical beam splitter 45 can then be eliminated.

In operation, the light intensity measurements for Io and Iear are made using the arrangement of FIG. 6 by illuminating the free space and tissue using light source 32. The light intensity is measured using photodetector 47. Because in this arrangement unpolarized light is used, it is possible that ambient light or stray light could affect the measurement. Simply making the measurements in a darkened environment, or physically shielding the system and the users' ear, for example, from ambient light, can improve the measurement by reducing any light at the photodetector 47 that was not sourced from component 32.

The rotation measurement is then made using component 31, polarizer 33 and 37, and photodetectors 35 and 47 as described above. The glucose concentration can then be determined using Equation 6. Thus the arrangement in FIG. 6 eliminates the need for a third photodetector and a third polarizer, but adds a second light source. In a further alternative arrangement that is contemplated by the inventors as forming an additional aspect of the present application, the polarizer 33 can be movable and can be inserted into the light path for the rotation measurements, while it is not in the light path for the path length measurements (for collecting the intensity readings Io and Iear).

Although the example arrangements have been described in detail, it should be understood that various changes, substitutions and alterations can be made herein without departing from the spirit and scope of the application as defined by any appended claims.

In an aspect of the present application, a method for performing non-invasive optical measurements includes: providing an optical energy source spaced from a first photo-detector by a sensing area; transmitting energy from the optical energy source across the sensing area and onto the first photo-detector; storing a first reading corresponding to a light intensity observed by the first photo-detector; subsequently, introducing a container of solution into the sensing area, the solution including an optically active substance; transmitting energy from the optical energy source, the sensing area including the container, and onto the first photo-detector; storing a second reading corresponding to the light intensity observed by the first photo-detector; determining a ratio of the first reading to the second reading; and determining a path length L by computing: $L=\ln(\text{ratio})/\mu$ where $\mu$ is an absorption constant of the optical energy in the solution and container.

In a further aspect of the present application, the method described above further includes transmitting optical energy from the optical energy source through a first polarizer and through the container and through a second polarizing device onto a second photo-detector; receiving the optical energy from the optical energy source through the first polarizer and onto a reference photo-detector; determining a change in polarization by observing a difference between a light intensity received at the second photo-detector and a light intensity at the reference photo-detector, the difference corresponding to an angle of rotation $\Theta$; and computing a concentration of an optically active compound in the solution as: $C=(\alpha^{*}(\ln(\text{ratio})/\mu)\Theta)$, where $\alpha$ is a rotation constant. In still a further method arrangement, the methods above further include determining a change in polarization which further includes measuring a voltage difference corresponding to the difference between the light intensity received at the second photo-detector and the reference photo-detector.

In another arrangement of the present application, the methods above are performed and further the optically active substance is glucose. In an alternative arrangement, the methods above are performed wherein the solution is human blood. In still another arrangement, the methods described above are performed wherein the container is human tissue.

In yet another arrangement of the present application, the methods above include wherein the container further comprises a portion of a human ear.

In still another arrangement, the methods above are performed wherein the portion of the human ear further comprises an anti-helix portion. In yet another arrangement, the tissue further comprises a portion of a human hand.

In another arrangement of the present application, the methods above are performed, wherein the container further comprises a glass container.

In another arrangement of the present application, the methods above are performed, and a third polarizer is provided between a second optical steering device and a third photodetector, wherein the first and third linear polarizers container further comprise matching polarizers.

In still another additional arrangement, the first and second optical steering devices are optical beam splitters.

In still another arrangement of the present application, an apparatus for non-invasive concentration measurement includes an optical energy source spaced from a first photo-detector by a sensing area; a first polarizer placed between the optical energy source and the sensing area; a first optical steering device between the sensing area and the first photo-detector, the first optical steering device outputting a reference signal to the first photo-detector and outputting a second light signal; a second photo-detector placed to receive the second light signal; a second polarizer placed between the first optical steering device and the second photo-detector to receive the second light signal and to output a polarized light signal; a second optical steering device disposed between the first optical steering device and the first photo-detector, outputting the reference signal and an absorption light signal; and a third photo-detector positioned to receive the absorption light signal; wherein the first photo-detector and the second photo-detector are arranged to receive the reference signal and the polarized light signal from the first optical steering device at a ninety degree angle, and the first photo-detector and the third photo-detector are arranged to receive the reference signal and the absorption light signal at a ninety degree angle.

In further arrangements, the above apparatus further includes a container disposed in the sensing area including a solution with a sugar in a concentration. In yet another arrangement, in the apparatus above, the optical energy source further comprises an LED. In still another arrangement, in the apparatus above, the LED further comprises a red LED. In yet another alternative arrangement, in the apparatus above, the photo-detectors further comprise photodiodes. In still another alternative arrangement, in the apparatus above, the first polarizer and a third polarizer between the second optical steering device and the third photo-detector are at zero degrees. In yet another apparatus arrangement of the present application, in the above apparatus, the second polarizer is at forty-five degrees.

In another alternative arrangement of the present application, an apparatus for non-invasive concentration measurement of a sugar in a solution includes: an optical energy source spaced from a first photo-detector by a sensing area; a first polarizer placed between the optical energy source and the sensing area; a first optical steering device between the sensing area and the first photo-detector, the first optical steering device outputting a polarized light signal to the first photo-detector and outputting a second light signal; a second polarizer placed between the first optical steering device and the first photo-detector and transmitting the polarized light signal to the first photo-detector; a second optical steering device receiving the second light signal and outputting an absorption light signal and a reference light signal; a third polarizer device placed between the second optical steering device and a second photo-detector for receiving the absorption light signal through the third polarizer device; and a third photo-detector placed to receive the reference light signal from the second optical steering device.

In still another arrangement, in the apparatus above, the first polarizer and the third polarizer are at zero degrees. In another alternative arrangement, in the apparatus above, the second polarizer is at forty-five degrees. In still another additional arrangement, the first and second optical steering devices are optical beam splitters.

Moreover, the scope of the present application is not intended to be limited to the particular embodiments of the process, machine, manufacture, and composition of matter, means, methods and steps described in the specification. As one of ordinary skill in the art will readily appreciate from the disclosure, processes, machines, manufacture, compositions of matter, means, methods or steps, presently existing or later to be developed, that perform substantially the same function or achieve substantially the same result as the corresponding embodiments described herein may be utilized according to the embodiments and alternative embodiments. Accordingly, the appended claims are intended to include within their scope such processes, machines, manufacture, compositions of matter, means, methods, or steps.

What is claimed is:

1. A method for performing non-invasive optical measurements, comprising:
   providing at least one optical energy source spaced from a first photo-detector by a sensing area;
   transmitting energy from the at least one optical energy source through a first polarizer having a first reference polarization angular position, across the sensing area, and through a second polarizer having the same first reference polarization angular position and onto the first photo-detector;
   storing a first reading corresponding to a light intensity observed by the first photo-detector;
   subsequently, introducing a container of solution into the sensing area, the solution including an optically active substance;
   transmitting energy from the optical energy source through the first polarizer, across the sensing area including the container, through the second polarizer, and onto the first photo-detector;
   storing a second reading corresponding to the light intensity observed by the first photo-detector;
   determining a ratio of the first reading to the second reading; and
   determining a path length L by computing:

$L=\ln(\text{ratio})/\mu$ where $\mu$ is an absorption constant of the optical energy in the solution and container.

2. The method of claim 1, and further comprising:
   transmitting optical energy from at least the first optical energy source through a first polarizer and through the container and through a third polarizing device onto a second photo-detector;
   receiving the optical energy from the optical energy source through the first polarizer and onto a reference photo-detector;
   determining a change in polarization by observing a difference between a light intensity received at the second photo-detector and a light intensity at the reference photo detector, the difference corresponding to an angle of rotation $\Theta$; and
   computing a concentration of an optically active compound in the solution as:
   $C=(\alpha*\ln(\text{ratio})/\mu)/\Theta)$, where $\alpha$ is a rotation constant.

3. The method of claim 2, determining a change in polarization further comprises:
   measuring a voltage difference corresponding to the difference between the light intensity received at the second photo-detector and the reference photo-detector.

4. The method of claim 1, and further comprising:
   providing a second optical energy source spaced from the reference photodetector by the sensing area;
   using the energy transmitted from second optical energy source, measuring the light intensity of unpolarized light received at the first photo-detector and storing the measurement as the first reading;
   introducing a container containing an optically active substance into the sensing space; and
   using the energy transmitted from second optical energy source through the sample space including the container and the liquid, measuring the light intensity of unpolarized light received at the first photo-detector and storing the measurement as the second reading.

5. The method of claim 4, wherein the optically active substance is glucose.

6. The method of claim 1, wherein the solution is human blood.

7. The method of claim 6, wherein the container further comprises a portion of a human ear or a portion of a human hand.

8. The method of claim 7, wherein the portion of the human ear further comprises an anti-helix portion.

9. The method of claim 6, wherein the container further comprises a glass container.

10. The method of claim 1 wherein the container is human tissue.

11. An apparatus for non-invasive concentration measurement, comprising:
   at least one optical energy source spaced from a first photo-detector by a sensing area;
   a first polarizer placed between the at least one optical energy source and the sensing area;
   a first optical beam splitter device between the sensing area and the first photo-detector, the first optical beam splitter outputting a reference signal to the first photo-detector and outputting a second light signal;
   a second photo-detector placed to receive the second light signal;
   a second polarizer placed between the first optical beam splitter and the second photo-detector to receive the second light signal and to output a polarized light signal;
   wherein the first photo-detector and the second photo-detector are arranged to receive the reference signal and the polarized light signal from the first beam splitter, respectively.

12. The apparatus of claim 11, and further comprising:
   a container disposed in the sensing area including a solution with a sugar in a concentration.

13. The apparatus of claim 11, wherein the at least one optical energy source further comprises an LED.

14. The apparatus of claim 13, wherein the LED further comprises a red LED.

15. The apparatus of claim 14, wherein the photo-detectors further comprise photodiodes.

16. The apparatus of claim 11, and further comprising:
   a second optical energy source spaced from the first photo-detector by the sensing area and positioned away from the first polarizer.

17. The apparatus of claim 16, wherein the second optical energy source is configured to transmit unpolarized light that traverses the sensing space and is received by the first photo-detector.

18. An apparatus for non-invasive concentration measurement of a sugar in a solution, comprising:
   an optical energy source spaced from a first photo-detector by a sensing area;
   a first polarizer placed between the optical energy source and the sensing area;
   a first optical beam splitter device between the sensing area and the first photo-detector, the first optical beam splitter outputting a polarized light signal to the first photo-detector and outputting a second light signal;
   a second polarizer placed between the first optical beam splitter and the first photo-detector and transmitting the polarized light signal to the first photo-detector;
   a second optical beam splitter device receiving the second light signal and outputting an absorption light signal and a reference light signal;
   a third polarizer device placed between the second optical beam splitter device and a second photo-detector for receiving the absorption light signal through the third polarizer device; and
   a third photo-detector placed to receive the reference light signal from the second optical beam splitter device.

19. The apparatus of claim 18, wherein the first polarizer and the third polarizer are at a same reference polarization angle.

20. The apparatus of claim 18, wherein the second polarizer is at forty-five degrees.

* * * * *